US006114323A

United States Patent [19]
Cerami et al.

[11] Patent Number: 6,114,323
[45] Date of Patent: *Sep. 5, 2000

[54] METHODS FOR INHIBITING THE ADVANCED GLYCOSYLATION OF PROTEINS

[75] Inventors: Anthony Cerami, New York, N.Y.; Peter C. Ulrich, Old Tappan, N.J.; Michael A. Brownlee, New York, N.Y.

[73] Assignee: The Rockefeller University, New York, N.Y.

[ * ] Notice: This patent is subject to a terminal disclaimer.

[21] Appl. No.: 09/215,612

[22] Filed: Dec. 17, 1998

Related U.S. Application Data

[63] Continuation of application No. 08/784,861, Jan. 16, 1997, Pat. No. 5,852,009, which is a continuation-in-part of application No. 08/487,059, Jun. 7, 1995, Pat. No. 5,612,332, which is a division of application No. 08/274,243, Jul. 13, 1994, abandoned, which is a division of application No. 07/889,141, May 27, 1992, Pat. No. 5,356,895, which is a division of application No. 07/605,654, Oct. 30, 1990, Pat. No. 5,140,048, which is a continuation-in-part of application No. 07/264,930, Nov. 2, 1988, Pat. No. 4,983,604, which is a continuation-in-part of application No. 07/119,958, Nov. 13, 1987, Pat. No. 4,908,446, which is a continuation-in-part of application No. 06/798,032, Nov. 14, 1985, Pat. No. 4,758,583, which is a continuation-in-part of application No. 06/590,820, Mar. 19, 1984, Pat. No. 4,665,192.

[51] Int. Cl.[7] .................................................. A01N 43/46

[52] U.S. Cl. ................................ 514/212.01; 514/237.8; 514/238.5; 514/514; 514/331; 514/399; 514/561; 514/531

[58] Field of Search ................................ 514/212, 237.8, 514/238.5, 331, 399, 561, 631, 212.1

[56] References Cited

U.S. PATENT DOCUMENTS

| | | | |
|---|---|---|---|
| 2,258,321 | 10/1941 | Ericks | 564/227 |
| 2,289,541 | 7/1942 | Bricks et al. | 564/227 |
| 2,300,570 | 11/1942 | Heuser et al. | 564/227 |
| 2,375,659 | 5/1945 | Jones et al. | 564/227 |
| 2,721,217 | 10/1955 | Peters et al. | 564/227 |
| 2,928,829 | 3/1960 | Mull | 564/227 X |
| 2,951,843 | 9/1960 | Haack et al. | 564/227 X |
| 3,006,913 | 10/1961 | Mull | 564/227 X |
| 3,053,732 | 9/1962 | Greenhalgh | 564/227 X |
| 3,055,882 | 9/1962 | Mull | 564/227 X |
| 3,055,883 | 9/1962 | Mull | 564/227 X |
| 3,081,222 | 3/1963 | Hagemann et al. | 548/315 |
| 3,098,066 | 7/1963 | Mull | 564/227 X |
| 3,101,336 | 8/1963 | James et al. | 564/227 X |
| 3,178,433 | 4/1965 | Mull | 564/227 X |
| 3,183,241 | 5/1965 | Oja | 564/227 X |

(List continued on next page.)

FOREIGN PATENT DOCUMENTS

| | | |
|---|---|---|
| 0 158 020 | 2/1985 | European Pat. Off. . |
| 0 222 313 | 11/1986 | European Pat. Off. . |
| 0 325 936 | 1/1989 | European Pat. Off. . |
| 316852 | 5/1989 | European Pat. Off. . |
| 327919 | 8/1989 | European Pat. Off. . |
| 2059975 | of 0000 | France . |
| 2029707 | 12/1970 | Germany . |
| 3040993 | 6/1982 | Germany . |
| 63-287492 | of 0000 | Japan . |
| 64-56614 | of 0000 | Japan . |
| 1036987 | of 0000 | United Kingdom . |
| 809165 | 5/1957 | United Kingdom . |
| 952194 | 12/1961 | United Kingdom . |
| 1274668 | 6/1968 | United Kingdom . |
| 1458636 | 9/1974 | United Kingdom . |
| WO 92/07560 | 5/1992 | WIPO . |

OTHER PUBLICATIONS

Flier et al. (1988) New Eng. J. Med. 318:1315–21.
Acharya et al. 1988. Biochemistry 27(12): 4522–9.
Brownlee et al. 1986. Science 232: 1629–32.
Brownlee et al. 1984. Ann. Int. Med. 101: 527–37.
Brownlee et al. 1983. J. Exp. Med. 158: 1739–44.
Bunn et al. 1975. Biochem. Biophys. Res. Comm. 67: 103–9.
Ebetino et al. 1962. J. Org. Chem. 27: 188–91.
Kohn et al. 1984. Diabetes 33(1): 57–9.
Lindberg and Tornqvist. 1966. Acta. Obst. Gynec. Scand. 45: 131–9.
Maillard. C.R. Acad. Sci. 154: 66–8. (1912).
Monnier et al. 1984. Proc. Natl. Acad. Sci. 81: 583–7.
Monnier and Cerami. 1983. in Maillard Reaction in Food and Nutrition. Waller, ed. American Chemical Society 215: 431–49.
Monnier and Cerami. 1983. Biochem. Biophys. Acta. 760: 97–103.
Monnier and Cerami. 1982. Clin. Endocrinol. Metab. 11: 431–52.
Monnier and Cerami. 1981. Science 211: 491–3.
Murdock et al. 1982. J. Med. Chem. 25: 505–18.
Ponger et al. 1984. Proc. Natl. Acad. Sci. USA 81: 2684–8.
Stoner et al. 1985. Agents and Actions 17: 5–9.
Sundberg et al. 1990. J. Med. Chem. 33: 298–307.
Tai et al. 1984. J. Med. Chem. 27: 236–8.
Ebetino et al. 1964. J. Org. Chem. 29: 2582–5.
Eble et al. 1983. J. Biol. Chem. 258: 9406–12.
Finot. 1982. in Food and Nutritional Aspects. Feeney and Whitaker, eds. American Chemical Society 198: 91–124.
Godfrey. 1962. "The synthesis of heterocyclic compounds from urea derivatives." Doctoral Dissertation. U. of London.
Hollis et al. 1985. Diabetologia 28: 282–85.
Koenig et al. 1977. J. Biol. Chem. 252: 2992–7.
Potekhin et al. 1973. Zhurnal Organicheskoi Khimii 9: 1180–6.

Primary Examiner—Floyd D. Higel
Attorney, Agent, or Firm—Klauber & Jackson

[57] ABSTRACT

The present invention relates to methods for inhibiting protein aging. Accordingly, methods are disclosed for treating an animal to inhibit the formation of advanced glycosylation end products of target proteins with the animal by adminstering a pharmaceutical composition comprising an agent capable of reacting with the carbonyl moiety of the early glycosylation product, whereby the subsequent crosslinking of the early glycosylation product is inhibited. Agents of the present invention comprise aminoguanidine, its pharmaceutically acceptable salts, and mixtures thereof.

32 Claims, 5 Drawing Sheets

U.S. PATENT DOCUMENTS

| | | | |
|---|---|---|---|
| 3,200,111 | 8/1965 | Paquette | 544/162 |
| 3,201,459 | 8/1965 | Coda et al. | 564/227 X |
| 3,202,710 | 8/1965 | Bolger | 564/227 X |
| 3,283,003 | 11/1966 | Jack et al. | 564/227 X |
| 3,291,829 | 12/1966 | Mull | 564/227 X |
| 3,317,545 | 5/1967 | Albrecht et al. | 564/227 X |
| 3,320,195 | 5/1967 | Braun | 564/227 X |
| 3,364,220 | 1/1968 | Biel et al. | 564/227 X |
| 3,506,680 | 4/1970 | Berger et al. | 564/227 X |
| 3,681,504 | 8/1972 | Johnston et al. | 564/227 X |
| 3,803,324 | 4/1974 | Winter et al. | 564/227 X |
| 3,978,060 | 8/1976 | Forsythe et al. | 514/601 |
| 3,980,774 | 9/1976 | Hegarty et al. | 514/614 |
| 3,991,209 | 11/1976 | Forsythe et al. | 514/601 |
| 4,161,541 | 7/1979 | Rasmussen | 564/227 X |
| 4,271,190 | 6/1981 | Bertelmann et al. | 564/227 X |
| 4,471,137 | 9/1984 | Barton et al. | 564/227 X |
| 4,544,759 | 10/1985 | Hlavaka et al. | 564/227 X |
| 4,665,192 | 5/1987 | Cerami et al. | 548/336 |
| 4,680,300 | 7/1987 | Nelson et al. | 564/227 X |
| 4,731,383 | 3/1988 | Erczi et al. | 564/227 X |
| 4,758,583 | 7/1988 | Cerami et al. | 514/399 |
| 4,908,446 | 3/1990 | Ulrich et al. | 540/553 |
| 4,983,604 | 1/1991 | Ulrich et al. | 514/238.5 |
| 5,006,523 | 4/1991 | Atwal | 564/227 X |
| 5,140,048 | 8/1992 | Ulrich et al. | 514/601 |
| 5,189,046 | 2/1993 | Burch et al. | 564/227 X |
| 5,196,450 | 3/1993 | Sjoerdsma et al. | 564/227 X |
| 5,296,498 | 3/1994 | Malen et al. | 514/401 |
| 5,336,689 | 8/1994 | Weber et al. | 564/227 X |
| 5,356,895 | 10/1994 | Ulrich et al. | 514/255 |
| 5,612,332 | 3/1997 | Wagle et al. | 514/212 |
| 5,852,009 | 12/1998 | Cerami et al. | 514/212 |

Covalent Trapping of BSA by Nonenzymatically Glycosylated Collagen

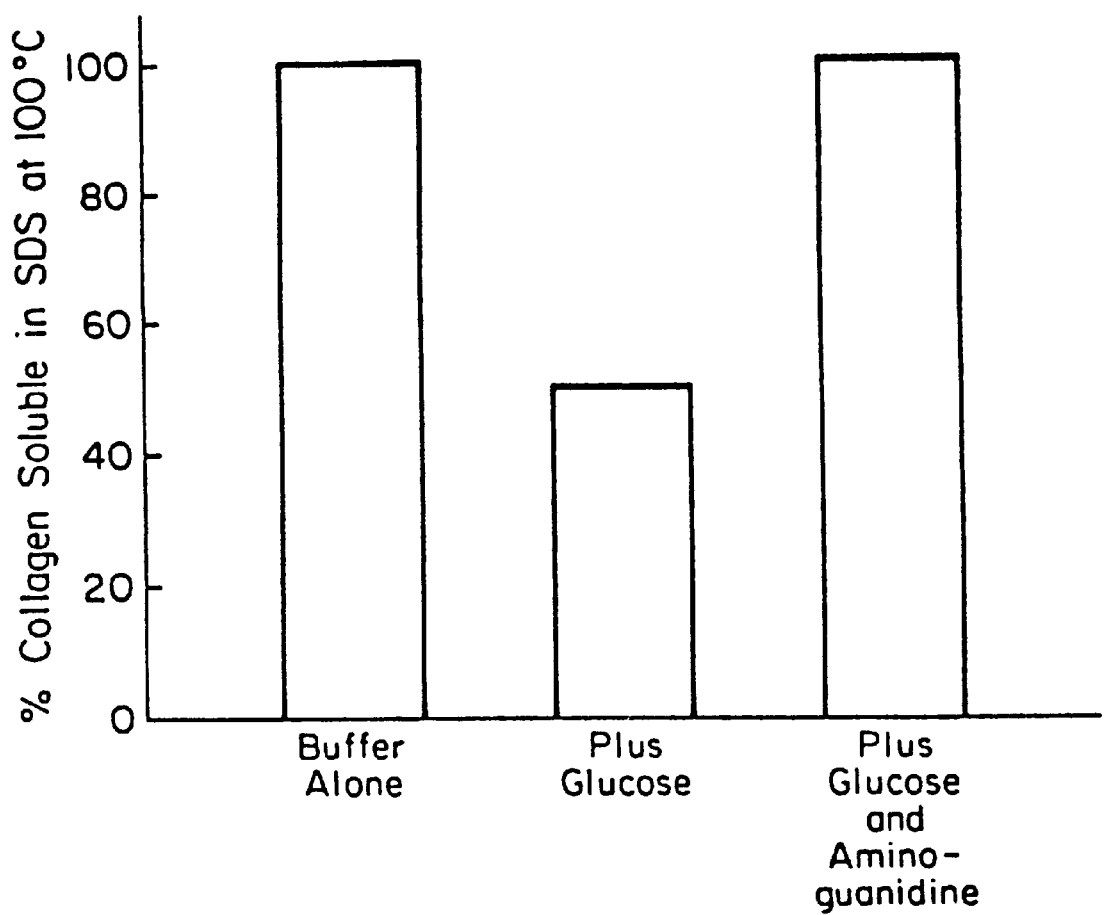

Inhibition of Advanced Glycosylation Product Formation *in vivo*

METHODS FOR INHIBITING THE ADVANCED GLYCOSYLATION OF PROTEINS

CROSS REFERENCE TO RELATED APPLICATIONS

The present application is a Continuation of application Ser. No. 08/784,861, filed Jan. 16, 1997, now U.S. Pat. No. 5,852,009, which is a Continuation-in-part of application Ser. No. 08/487,059, filed Jun. 7, 1995, now U.S. Pat. No. 5,612,332, which is a Division of application Ser. No. 08/274,243, filed Jul. 13, 1994, now abandoned; which is a Division of application Ser. No. 07/889,141, filed May 27, 1992, now U.S. Pat. No. 5,356,895; which is a division of U.S. Ser. No. 07/605,654, filed Oct. 30, 1990, now U.S. Pat. No. 5,140,048; which is a Continuation-In-Part of Ser. No. 07/264,930, filed Nov. 2, 1988, now U.S. Pat. No. 4,983,604; which is a Continuation-In-Part of application Ser. No. 07/119,958, filed Nov. 13, 1987, now U.S. Pat. No. 4,908,446; which is a Continuation-In-Part of application Ser. No. 06/798,032, filed Nov. 14, 1985 and now U.S. Pat. No. 4,758,583; which is a Continuation-In-Part of application Ser. No. 06/590,820, filed Mar. 19, 1984, and now U.S. Pat. No. 4,665,192. Applicants claim the benefits of these Applications under 35 U.S.C. §120.

This invention was made with partial assistance from grants from the National Institutes of Health and the Brookdale Foundation.

RELATED PUBLICATIONS

The Applicants are co-authors of the following articles directed to the subject matter of the present invention: "COVALENT ATTACHMENT OF SOLUBLE PROTEINS BY NONENZYMATICALLY GLYCOSYLATED COLLAGEN; ROLE IN THE IN SITU FORMATION OF IMMUNE COMPLEXES. Brownlee, M., Pongor, S., Cerami, A., *J. Exp. Med.*, 158, pp. 1739–1744 (1983); "AGING OF PROTEINS: ISOLATION AND IDENTIFICATION OF A FLUORESCENT CHROMOPHORE FROM THE REACTION OF POLYPEPTIDES WITH GLUCOSE", Pongor, S., Ulrich, P., Bencsath, A. A., and Cerami, A., *Proc. Natl. Acad. Sci. USA*, 81, pp. 2682–2688 (1984); and "ADVANCED GLYCOSYLATION END PRODUCTS IN TISSUE AND THE BIOCHEMICAL BASIS OF DIABETIC COMPLICATIONS", Brownlee, M., Cerami. A., and Vlassara, H., *The New England Journal of Medicine*, 318, pp. 1315–1321 (1988). All of the above publications are incorporated herein by reference.

BACKGROUND OF THE INVENTION

The present invention relates generally to the aging of proteins resulting from reaction of glucose, and particularly to the nonenzymatic glycosylation of proteins and subsequent reactions leading to advanced glycosylation end products, and to methods and agents for their inhibition.

The reaction between glucose and proteins has been known for some time. Its earliest manifestation was in the appearance of brown pigments during the cooking of food, which was identified by Maillard in 1912. who observed that glucose or other reducing sugars react with amino acids to form adducts that undergo a series of dehydrations and rearrangements to form stable brown pigments Maillard, L. D. *C.R. Acad. Sci.*, 154, pp. 66–68 (1912).

In the years that followed the initial discovery by Maillard, food chemists studied the hypothesized reaction in detail and determined that stored and heat treated foods undergo nonenzymatic browning as a result of the reaction between glucose and the polypeptide chain, and that the proteins are resultingly crosslinked and correspondingly exhibit decreased bioavailability. At this point, it was determined that the pigments responsible for the development of the brown color that develops as a result of protein glycosylation possessed characteristic spectra and fluorescent properties; however, the chemical structure of the pigments had not been specifically elucidated.

The reaction between reducing sugars and food proteins discussed above was found in recent years to have its parallel in vivo. Thus, the nonenzymatic reaction between glucose and the free amino groups on proteins to form a stable amino, 1-deoxy ketosyl adduct, known as the Amadori product, has been shown to occur with hemoglobin, wherein a rearrangement of the amino terminal of the β-chain of hemoglobin by reaction with glucose, forms the adduct known as hemoglobin $A_{ic}$. The reaction has also been found to occur with a variety of other body proteins, such as lens crystallins, collagen and nerve proteins. See Bunn. H. F., Haney, D. N., Gabbay, K. H. and Gallop, P. H., *Biochem. Biopllys. Res. Comm.*, 67, pp. 103–109 (1975); Koenig, R. J., Blobstein, S. H. and Cerami, A., *J. Biol. Chem.*, 252, pp. 2992–2997 (1975); Monnier, V. M. and Cerami, A. in *Maillard Reaction in Food and Nutrition*, ed. Waller, G. A., American Chemical Society, 215, pp. 431–448 (1983); and Monnier, V. M. and Cerami, A., *Clinics in Endocrinology and Metabolism*, 11, pp. 431–452 (1982).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years. See Monnier, V. M. and Cerami, A., *Science*, 211, pp. 491–493 (1981); Monnier, V. M. and Cerami, A., *Biochem. Biophys. Acta*, 760, pp. 97–103 (1983); and Monnier, V. M., Kohn, R. R. and Cerami, A., "Accelerated Age-Related Browning of Human Collagen in Diabetes Mellitus", *Proc. Natl. Acad. Sci.*, 81, pp. 583–587 (1984). Interestingly, the aging of collagen can be mimicked in vitro by the crosslinking induced by glucose; and the capture of other proteins and the formation of adducts by collagen, also noted, is theorized to occur by a crosslinking reaction, and is believed to account for the observed accumulation of albumin and antibodies in kidney basement membrane. See Brownlee, M., Pongor, S. and Cerami, A., *J. Exp. Med.*, 158, pp. 1739–1744 (1983); and Kohn, R. R., Cerami, A. and Monnier, V. M., *Diabetes*, 33(1), pp. 57–59 (1984).

Recently, the role of other naturally-occurring reducing sugars, including fructose, in nonenzymatic cross-linking has been discussed. Specifically, Suarez et al. "Administration of an Aldose Reductase Inhibitor Induces a Decrease of Collagen Fluorescence in Diabetic Rats", *J. Clin. Invest.*, 82, pp. 624–627 (1988) have shown that fructose levels are elevated in diabetes as a result of the elevated glucose being channeled through the polyol pathway, first to sorbitol then to fructose. These investigators also showed that the ability of fructose to cause nonenzymatic crosslinking as measured by collagen fluorescence, is 10 times greater than that of glucose. Because the methods and agents of the present invention block nonenzymatic crosslinking mediated by any of the reactive sugars, they are expected to prevent fructose-mediated crosslinking as well. Cross-linking caused by other reactive sugars present in vivo or in foodstuffs, including ribose and galactose, would also be prevented by the methods and compositions of the present invention.

In parent application Ser. No. 590,820 (now U.S. Pat. No. 4,665,192) and in Pongor, S. M., et al., supra, both incorporated herein by reference, a fluorescent chromophore was isolated and identified which was found to be present in certain browned polypeptides such as bovine serum albumin and poly-L-lysine, and was assigned the structure 2-(2-furoyl)-4(5)-2(furanyl)-1H-imidazole. The compound was found to exist in a tautomeric state and has incorporated in its structure two peptide-derived amine nitrogens. The incorporation of these amine nitrogens and two glucose residues in the compound suggested that its peptide-bound precursor may be implicated in the in vivo crosslinking of proteins by glucose, which is observed in the late stage of the Maillard process. [See Chang, J. C. F., Ulrich, P. C., Bucala, R. and Cerami, A., *J. Biol. Chem.,* 260, pp. 7970–7974 (1985)]. This chromophore made possible the identification of the advanced glycosylation end products and assisted additional investigations seeking to clarify the protein aging process and to identify the specific chemistry involved in order to develop methods and agents for its inhibition. It is to this purpose that the present Application is directed.

More recently, other advanced glycosylation products have been identified, such as Farmar et al., U.S. Ser. No. 097,856, filed Sep. 17, 1987, pyrraline (Hayase et al., "Aging of Proteins: Immunological Detection of a Glucose-derived Pyrrole Formed during Maillard Reaction in Vivo", *J. Biol. Chem.,* 263, pp. 3758–3764 (1989)), pentosidine (Sell, D. and Monnier V. "Structure Elucidation of a Senescence Cross-link from Human Extracellular Matrix" *J. Biol. Chem.,* 264, pp. 21597–21602 (1989)). Formation of these advanced glycosylation products would be inhibited by the methods and agents of the present invention. The present invention is not restricted to any of these advanced glycosylation endproducts specifically, but to the general process of their formation as a result of the reaction of proteins with sugars.

SUMMARY OF THE INVENTION

In accordance with the present invention, a method and associated agents are disclosed for the inhibition of protein aging. In particular, agents for inhibiting protein aging due to the formation of advanced glycosylation end products may be selected from those materials capable of reacting with the early glycosylation product from the reaction of glucose with proteins and preventing further reactions. Thus, for example, compounds or compositions having active nitrogen-containing substituents such as hydrazine groups, have been theorized to be suitable and compounds such as aminoguanidine and α-hydrazinohistidine have been found to be suitable. These agents appear to react with the early glycosylation product at its reactive carbonyl and thereby prevent the same from later forming the advanced glycosylation end products which lead to protein crosslinks. A particularly preferred agent comprises aminoguanidine and its salts.

The present invention also relates to a method for inhibiting protein aging by contacting the initially glycosylated protein at the stage of the early glycosylation product with a quantity of one or more of the agents of the present invention. In the instance where the present method has industrial application, one or more of the agents may be applied to the proteins in question, either by introduction into a mixture of the same in the instance of a protein extract, or by application or introduction into foodstuffs containing the protein or proteins, all to prevent premature aging and spoilage of the particular foodstuffs.

In the instance where the present method has therapeutic application, the animal host intended for treatment may have administered to it a quantity of one or more of the agents in a suitable pharmaceutical form. Administration may be accomplished by known techniques, such as oral, topical and parenteral techniques such as intradermal, subcutaneous, intravenous or intraperitoneal injection, as well as by other conventional means. Administration of the agents may take place over an extended period of time at a dosage level of, for example, up to about 25 mg/kg of host body weight. More particularly, the dosage level may range from 2–10 mg/kg, and may preferably range from 4–8 mg/kg.

The ability to inhibit the formation of advanced glycosylation end products carries with it significant implications in all applications where protein aging is a serious detriment. Thus, in the area of food technology, the retardation of food spoilage would confer an obvious economic and social benefit by making certain foods or marginal stability less perishable and therefore more available for consumers. Spoilage would be reduced as would the expense of inspection, removal and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, might be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as one of the sequelae of diabetes. Consequently, the ability to either retard or substantially inhibit the formation of advanced glycosylation end products carries the promise of favorably treating a significant adverse effect of diabetes and, of course, improving the quality and perhaps duration of animal life.

Accordingly, it is a principal object of the present invention to provide a method for inhibiting the extensive cross-linking of proteins that occurs as an ultimate consequence of the reaction of the proteins with glucose or other reducing sugars, by correspondingly inhibiting the formation of advanced glycosylation end products.

It is a further object of the present invention to provide a method as aforesaid which is characterized by a reaction with early glycosylation products.

It is a further object of the present invention to provide a method as aforesaid which prevents the rearrangement and cross-linking of the said early glycosylation products to form the said advanced glycosylation end products.

It is a yet further object of the present invention to provide agents capable of participating in the reaction with the said early glycosylation products in the method as aforesaid.

It is a still further object of the present invention to provide therapeutic methods of treating the adverse consequences of protein aging, manifest in the embrittlement of animal protein and the browning and spoilage of foodstuffs.

Other objects and advantages will become apparent to those skilled in the art from a consideration of the ensuing description which proceeds with reference to the following illustrative drawings.

BRIEF DESCRIPTION OF THE DRAWINGS

FIG. 3A is a graph of the degree of solubilization of collagen incubated with glucose, with and without treatment with an agent of the present invention.

DETAILED DESCRIPTION OF THE PREFERRED EMBODIMENT

Figure 1:
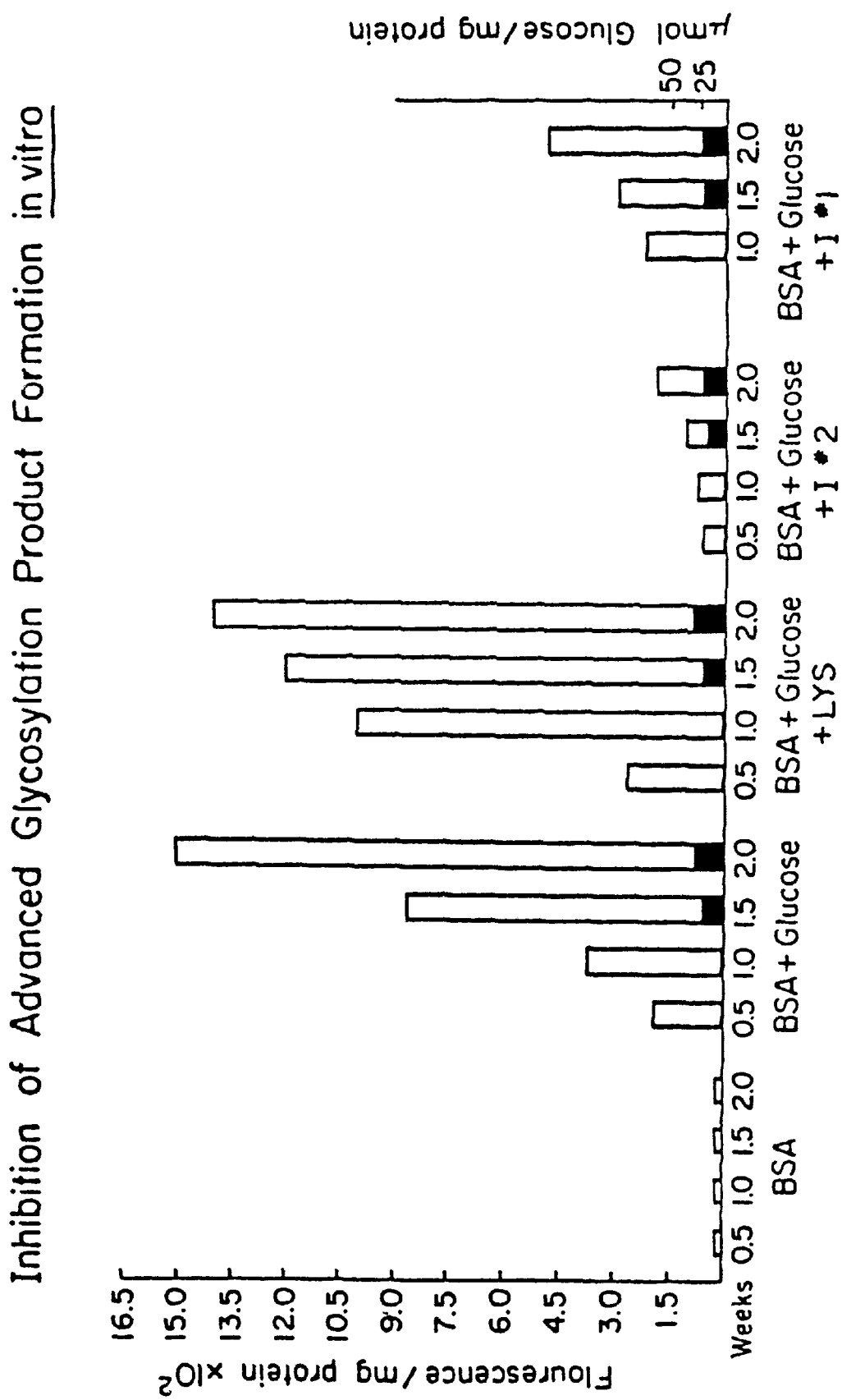
FIG. 1 is a graph showing the results of studies aimed at inhibiting the formation of advanced glycosylation end products in albumin which had been reacted with a quantity of glucose, on an in vitro basis.

In accordance with the present invention, compositions and associated methods have been developed which inhibit the formation of advanced glycosylation end products in a number of target proteins existing in both animals and plant material. In particular, the invention relates to compositions which may contain one or more agents that are capable of inhibiting the formation of advanced glycosylation end products on such target proteins, by reacting with the carbonyl moiety of the early glycosylation product that is formed by the initial glycosylation of the protein. A particularly preferred agent comprises aminoguanidine and its salts.

It is the carbonyl group located near the junction between sugar and protein segments of the early glycosylation product that is theorized to comprise an active site that causes the further cross-linking of the protein to form the advanced glycosylation end product, and likewise contributes to the entrapment of other proteins that is evident in the development in video of conditions such as skin wrinkling, certain kidney diseases, atherosclerosis, osteoarthritis and the like. Similarly, plant and animal material that undergoes nonenzymatic browning deteriorates and, in the case of foodstuffs, become spoiled or toughened and consequently, inedible. Thus, the reaction of the compounds of this invention with this carbonyl moiety is believed to inhibit the late stage Maillard effect and intervene in the deleterious changes described above.

The rationale of the invention is to use agents which block the post-glycosylation step, i.e., the formation of fluorescent chromophores such as that identified in Pongor, et al., supra and Farmar et al., supra, among others, whose presence is associated with, and leads to, the adverse sequelae of diabetes and aging. An ideal agent would prevent the formation of a chromophore and its associate cross-links of proteins to proteins and trapping of proteins on the other proteins, such as that which occurs in arteries and in the kidney.

The present invention does not attempt to prevent initial protein glycosylation, as it would be nearly impossible to use agents which prevent the reaction of glucose with protein amino groups. The agents that are capable of preventing initial glycosylation are likely to be highly toxic, and since the initial glycosylation comes to equilibrium in about three weeks, there is inadequate time available to achieve this objective. Instead, the ideal agent would prevent or inhibit the long-term, post-glycosylation steps that lead to the formation of the ultimate advanced glycosylation end products that are a direct cause of the pathology associated with aging and diabetes.

The chemical nature of the early glycosylation products with which the compounds of the present invention is believed to react are speculative. Early glycosylation products with carbonyl moieties which are involved in the formation of advanced glycosylation products, and which may be blocked by reaction with the compounds of the present invention, have been postulated. In one case, the reactive carbonyl moieties of Amadori products or their further dehydration and/or rearrangement products, may condense to form advanced glycosylation endproducts. Another proposed mechanism is the formation of reactive carbonyl compounds, containing one or more carbonyl moieties (such as glycoaldehyde or 3-deoxyglucosone) from the cleavage of Amadori or other early glycosylation products (see, for example, Gottschalk, A. (1972) in The Glycoproteins (Gottschalk, A., ed) Part A, pp. 141–157, Elsevier Publishing Co., New York, Reynolds T. M. (1965) *Adv. Food Res.*, 14, pp. 167–283), and by subsequent reactions with an amine or Amadori product to form carbonyl containing advanced glycosylation products such as the alkylformylglycosylpyrroles described by Farmar et al, supra.

Several investigators have studied the mechanism of advanced glycosylation product formation. In vitro studies by Eble et al., (1983), "Nonenzymatic Glucosylation and Glucose-dependent Cross-linking of Protein", *J. BIOL. CHEM.*, 258:9406–9412, concerned the crosslinking of glycosylated protein with nonglycosylated protein in the absence of glucose. Eble et al. sought to elucidate the mechanism of the Maillard reaction and accordingly conducted controlled initial glycosylation of RNAase as a model system, which was then examined under varying conditions.

In one aspect, the glycosylated protein material was isolated and placed in a glucose-free environment and thereby observed to determine the extent of cross-linking. Eble et al. thereby observed that cross-linking continued to occur not only with the glycosylated protein but with non-glycosylated proteins as well. One of the observations noted by Eble et al. was that the reaction between glucose and the protein material appeared to occur at the location on the protein chain of the amino acid lysine. Confirmatory experimentation conducted by Eble et al. in this connection demonstrated that free lysine would compete with the lysine on RNAase for the binding of glucose. Thus, it might be inferred from these data that lysine may serve as an inhibitor of advanced glycosylation; however, this conclusion and the underlying observations leading to it should be taken in the relatively limited context of the model system prepared and examined by Eble et al. Clearly, Eble et al. does not appreciate, nor is there a suggestion therein, of the discoveries that underlie the present invention, with respect to the inhibition of advanced glycosylation of proteins both in vitro and in vivo.

The experiments of Eble et al. do not suggest the reactive cleavage product mechanism or any other mechanism in the in vivo formation of advanced glycosylation endproducts in which glucose is always present. In fact, other investigators support this mechanism to explain the formation of advanced glycosylated endproducts in vivo (see for example Hayase et al, 1989, supra; Sell and Monnier, 1989, supra; Oimomi et al., *AGRIC. BIOL. CHEM.*, 53(6):1727–1728 (1989); and *Diabetes Research and Clinical Practice*, 6:311–313 (1989). The use of lysine as an inhibitor in the Eble et al. model system has no bearing upon the utility of the compounds of the present invention in the inhibition of advanced glycosylated endproducts formation in the presence of glucose in vivo and the amelioration of complications of diabetes and aging.

Accordingly, the compositions useful in the present invention comprise or contain agents capable of reacting with the active carbonyl intermediate of the early glycosylation product. Suitable agents include compounds having an active nitrogen-containing group or substituent such as a hydrazine group. Also, the agent of compound may be at least partially derived from an amino acid, including the esters and amides thereof, as compounds having this derivation are generally biocompatible with the target proteins to be contacted. For example, it has been earlier disclosed in parent applications to the present disclosure, that the agent may comprise a compound such as aminoguanidine, α-hydrazinohistidine and lysine, or mixtures of these agents or compounds. Each of these agents or compounds possesses an active nitrogen-containing substituent that is believed to react with the carbonyl of the early glycosylation product. Consequently, reaction of the agents with the glycosyl-lysine moiety of a protein would prevent this moiety from forming crosslinks with other groups. The agent of interest herein, however, is aminoguanidine and its pharmaceutically useful and acceptable salts.

Hollis and Strickberger (*Diabetologia* 28:282–5 [1985]) found that in vivo administration of the compound α-hydrazinohistidine, a known inhibitor of the enzyme histidine decarboxylase, reduces the accumulation of albumin in the aortas of rats. The authors proposed that the drug acted to reduce production of histamine in this tissue, and that histamine is therefore the mediator of low density lipoprotein accumulation which is implicated in atherosclerotic disease. In contrast, aminoguanidine is known to increase levels of histamine (See Lindberg et al., *Acta Obst. Gynecol. Scandinav.*, 45: 131–139, (1966)) and α-hydrazinohistidine and aminoguanidine therefore have opposing effects on histamine levels. It can therefore by seen that the findings that both α-hydrazinohistidine and aminoguanidine have efficacy in vivo and in vitro to reduce protein crosslinking rules out from consideration and consequently distinguishes the mechanism proposed by Hollis and Strickberger as the explanation of the manner in which the compounds of the present invention might work to reduce advanced glycosylation end product formation. Moreover, the findings of Hollis and Strickberger are distinguishable from the concept and application of the present invention because the mechanism of histamine synthesis suppression by α-hydrazinohistidine suggested by the authors is functionally distinct from the underlying concept of the present invention, and it is believed, may even be placed in question by the latter.

Thus, the agents of the present invention have been identified and tested on the basis of their ability to react with the carbonyl moiety of the early glycosylation product to form a highly stable adduct, and would not have been suggested from the work of Hollis and Strickberger.

The compound aminoguanidine is known to have low toxicity in animals. According to the 1978 Registry of Toxic Effects of Chemical Substances, aminoguanidine base has a $LD_{50}$, when administered subcutaneously of 1258 mg/kg in rats and 963 mg/kg in mice. The hydrochloride derivative had a $LD_{50}$, in rats of 2984 mg/kg when given subcutaneously. The latter compound exhibits very low toxicity.

In the instance where the composition of the present invention is utilized for in vivo or therapeutic purposes, it may be noted that the compounds or agents used therein are biocompatible. Pharmaceutical compositions may be prepared with a pharmaceutically effective quantity of the agents or compounds of the present invention and may include a pharmaceutically acceptable carrier, selected from known materials utilized for this purpose. Such compositions may be prepared in a variety of forms, depending on the method of administration. For example, aminoguanidine may be derivatized to the hydrochloride salt from the commercially available bicarbonate salt to improve its solubility and to make it less irritating for intraperitoneal injection. Also, a liquid form would be utilized in the instance where administration is by intravenous or intraperitoneal injection, while, inappropriate, tablets, capsules, etc., may be prepared for oral administration. For application to the skin a lotion or ointment may be formulated with the agent in a suitable vehicle, perhaps including a carrier to aid in penetration into the skin. Other suitable forms for administration to other body tissues are also contemplated.

For the purposes of this invention and as set forth above, equivalent compounds corresponding to the present agents are the biologically and pharmaceutically acceptable acid addition salts thereof. Such acid addition salts may be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic and related acids.

The present invention likewise relates to methods lor inhibiting the formation of advanced glycosylation end products, which comprise contacting the target proteins with the composition of the present invention. In the instance where the target proteins are contained in foodstuffs, whether plant of animal origin, these foodstuffs could have applied to them by various conventional means a composition containing the present agents. Likewise, in the instance where therapeutic applications are intended, the animals to be treated would have administered to them a regular quantity of the pharmaceutical composition of the present invention. Administration could take place, for example, daily, and an effective quantity of the agent or compound of the present invention could range up to 25 mg/kg of body weight of the animal. As stated above, a particular dosage range may be from 2–10 mg/kg, and a preferred range is from 4–8 mg/kg. A topical preparation may, for example, include up to 10% of the agent or composition in an ointment or lotion for application to the skin. Naturally, some variation in these amounts is possible, and the suggested amounts are provided in fulfillment of applicants' duty to disclose the best mode for the practice of the present invention.

As is apparent from a discussion of the environment of the present invention, the present methods and compositions hold the promise for arresting the aging of key proteins both in animals and plants, and concomitantly conferring both economic and medical benefits as a result thereof. In the instance of foodstuffs, the administration of the present composition holds the promise for retarding food spoilage thereby making foodstuffs of increased shelf life and greater availability to consumers. Replacement of currently-used preservatives, such as sulfur dioxide known to cause allergies and asthma in humans, with non-toxic biocompatible compounds is a further advantage of the present invention.

The therapeutic implications of the present invention relate to the arrest of the aging process which has, as indicated earlier, been identified in the aging of key proteins by advanced glycosylation and crosslinking. Thus, body proteins, and particularly structural body proteins such as collagen, elastin, lens proteins, nerve proteins and kidney glomerular basement membranes would all benefit in their longevity and operation from the practice of the present invention. The present invention thus reduces the incidence of pathologies involving the entrapment of proteins by crosslinked target proteins, such as retinopathy, cataracts, diabetic kidney disease glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies.

Protein crosslinking through advanced glycosylation product formation can decrease solubility of structural proteins such as collagen in vessel walls (see Brownlee et al., Science, 232, pp. 1629–1632, (1986)), and as well as trap serum proteins, such as lipoproteins to the collagen. Also, this may result in covalent trapping of extravasated plasma proteins in subendothelial matrix and reduction in susceptibility of both plasma and matrix proteins to physiologic degradation by enzymes. (See Brownlee et al., Diabetes, 35, Suppl. 1, p. 42A (1986).) For these reasons, the progressive occlusion of diabetic vessels induced by chronic hyperglycemia has been hypothesized to result from excessive formation of glucose-derived crosslinks. Such diabetic macrovascular changes and microvascular occlusion can be effectively prevented by chemical inhibition of advanced glycosylation product formation utilizing a composition and the methods of the present invention.

Other studies indicate that the development of chronic diabetic damage in target organs is primarily linked to hyperglycemia so that tight metabolic control would delay or even prevent end-organ damage. See Nicholls et al., Lab. Invest., 60(4), p. 486 (1989), which discusses the effects of islet isografting and aminoguanidine in murine diabetic nephropathy. These studies further evidence that aminoguanidine, an agent of the present invention, diminishes kidney glomerular basement membrane protein crosslinking in diabetic rats and extends the earlier studies of Brownlee et al., Science, 232, pp. 1629–1632 (1986) to this additional target organ of complication of diabetes. An additional study showed the reduction of immunoglobulin trapping in the kidney by aminoguanidine (Brownlee et al., Diabetes, 35, Suppl. 1, p. 42A (1986)).

Further evidence in the streptozotocin-diabetic rat model that aminoguanidine administration intervenes in the development of diabetic nephropathy was presented by Brownlee et al., 1988. supra, with regard to morphologic changes in the kidney which are hallmarks of diabetic renal disease. These investigators reported that the increased glomerular basement membrane thickness, a major structural abnormality characteristic of end-stage diabetic renal disease, was prevented with aminoguanidine.

Taken together, these data strongly suggest that inhibition of the formation of advanced glycosylation endproducts (AGE's), by the teaching of the present invention, may prevent late as well as early structural lesions due to diabetes, as well as changes during aging caused by the formation of AGE's.

Diabetes-induced changes in the deformability of red blood cells, leading to more rigid cell membranes, is another manifestation of cross-linking and aminoguanidine has been shown to prevent it in vivo.

Increased cross-linking of collagen in diabetic rats has shown to be prevented by aminoguanidine. Oxlund and Andreassen, "The increase in biochemical and biomechanical stability of collagen in diabetic rats is prevented by aminoguanidine treatment", European Association for the Study of Diabetes, Twenty-fifth Annual Meeting, p. 525A, Abstract No. 371, 1989 showed the effect when thermal stability of tendon fibers was assessed by breaking time in a urea bath, as well as mechanical strength. Soulis et al. "Aminoguanidine reduces tissue fluorescence but not albuminuria in diabetic rats". NIH Conference on the Maillard Reaction in Aging, Diabetes, and Nutrition, Bethesda, Md., Sep. 22–23, 1988, page 30) showed the same effect on collagen in the aorta, measured by fluorescence and solubility.

Giambione and Brownlee, "Aminoguanidine Treatment Normalizes Increased Steady-state Levels of Laminin B I mRNA in Kidneys of Long-term Streptozotocin-diabetic Rats" Diabetes 38, Supplement 2:83A Forty-ninth Annual Meeting, American Diabetes Association (1989) showed that aminoguanidine treatment to diabetic rats prevents the diabetes-induced increase in laminin MRNA in the kidney. This indicates that aminoguanidine may prevent overproduction of matrix, which leads to basement membrane thickening and morphologic and functional deterioration of vasculature in kidneys and other organs.

A further consequence of diabetes is the effect of hyperglycemia on bone matrix differentiation resulting in decreased bone formation usually associated with chronic diabetes. In animal models, diabetes reduces matrix-induced bone differentiation by 70% and in vitro models mimic this effect. Aminoguanidine prevents the decreased bone formation in this model.

The present invention will be better understood from a consideration of the following illustrative examples, reviewing the selection and testing of certain of the agents of the present invention on both an in vitro and in vivo basis.

EXAMPLE I

To measure the ability of certain of the agents of the present invention to inhibit the production of advanced glycosylated end products in vitro, albumin and glucose were incubated together for two weeks in the presence of several test agents. Samples were taken at regular intervals for analysis. Advanced glycosylation end products were measured as appearance of fluorescent compounds, and early glycosylation products were measured by incorporation of radiolabeled glucose into albumin. Reaction conditions were as follows. Each mixture contained 6 mg/mL bovine serum albumin, 200 mM glucose, 200 mM test agent (either aminoguanidine hydrochloride, $\alpha$-hydrazinohistidine, or lysine), and approximately $9.5 \times 10^6$ Counts per minute of 14 C-glucose in 0.5M phosphate buffer, pH7.6. The radiolabeled glucose was prepurified before use to eliminate breakdown products which might react with the albumin and lead to an erroneous indication of the degree of early glycosylation product formation. Reaction mixtures were incubated at 37° C., and samples were taken after 0.5, 1.0, 1.5, and 2 weeks. Control mixtures lacked glucose or agent.

After the incubation periods, samples were treated as follows. After dialysis to remove all unbound glucose, the amount of protein present was measured with a standard dye-binding assay. The amount of glucose which became bound to the albumin, a measure of early glycosylation products, was determined by precipitating albumin with trichloroacetic acid and measuring the radioactivity of the bound glucose using scintillation counting. Advanced glycosylation end products were quantitated by determining the fluorescence of the albumins described in parent application Ser. No. 590,820, and as described by Pongor et al., supra. Spectral measurements on excitation and emission maxima were made on all samples to ensure that these values had not been shifted as a result of adduct formation with inhibitors.

The results of this experiment are expressed graphically in FIG. 1. For each sample, incorporation of radiolabeled glucose is indicated by the solid portion of the bar, and fluorescence is indicated in the open portion of the bar. All values are expressed as per milligram of albumin. In all further discussions, aminoguanidine refers to the hydrochloride derivative.

The results show that the glucose and albumin react to form a large amount of fluorescent advanced glycosylation end products after 0.5, 1, 1.5 and 2 weeks of incubation ("GLUCOSE+BSA"). Inclusion of 200 mM aminoguanidine dramatically reduced by as much as eightfold with formation of fluorescent compounds, by comparison with the control samples after a two-week incubation ("BSA +GLUCOSE+I#2). Inclusion of 200 mM α-hydrazinohistidine also reduced formation of advanced glycosylation end products as measured by fluorescence ("BSA+GLUCOSE+I#1). Lysine appeared to cause an increase in fluorescent compound formation ("BSA+ GLUCOSI+LYS"), but as will be seen in the next experiment, it had the ability to reduce protein crosslinking. The amount of early glycosylation end products, as measured by glucose incorporation, was nearly unchanged in all reactions. The control incubation without glucose showed little development of fluorescent products (A).

These results show that aminoguanidine, and to a lesser extent, α-hydrazinohistidine, reduce the formation of fluorescent compounds when glucose and albumin react over time, and indicate that these two agents reduce the amount of advanced glycosylation end products which form. The agents do not alter the formation of early glycosylation products.

EXAMPLE II

To more precisely measure the effect of the agents on the inhibition of protein crosslinking, an assay system was devised to measure the extent of in vitro binding of a soluble protein to an insoluble protein. This assay system mimics the events which occur in tissues in which serum proteins become bound to proteins in extravascular matrix and which lead to accumulation of protein and narrowing of vessel lumina in several other tissues. These events in vivo give rise to kidney disease and atherosclerotic disease, and lead to the pathologies associated with diabetes and aging.

To measure protein trapping (i.e., binding or accumulation), gelatin (collagen) was coupled to activated agarose beads (Affigel 10, Bio-Red Laboratories) by routine methods. After coupling, all remaining active sites on the beads were quenched by reaction with glycine ethyl ester.

The beads were incubated for two weeks with bovine serum albumin and 400 mN glucose-6-phosphate, a more reactive form of glucose which forms early glycosylation products with proteins more rapidly than does glucose. Also included in some experiments were the test agents, aminoguanidine, α-hydrazinohistidine, or lysine, at a concentration of 200 mN. The bovine serum albumin was radioiodinated so that the amount which became bound to the beads could be measured. The amount of radiolabel that became bound to the beads in a direct measure of protein trapping.

After a two-week incubation of the reaction mixtures at 37° C., the beads were washed extensively with chaotropic agents and the covalently bound radioactivity was determined. The results are set forth in FIG. 2.

The left bar shows the control level of radiolabel incorporated into the beads in the absence of glucose-6-phosphate and in the absence of any test agents ("CONTROL COLLAGEN"). The second bar shows the high amount of incorporation in the presence of glucose-6-phosphate ("NEG. COLLAGEN"). This is likened to the presence of high concentrations of glucose in the blood of uncontrolled patients with diabetes and the pathological sequelae which result.

Figure 2:
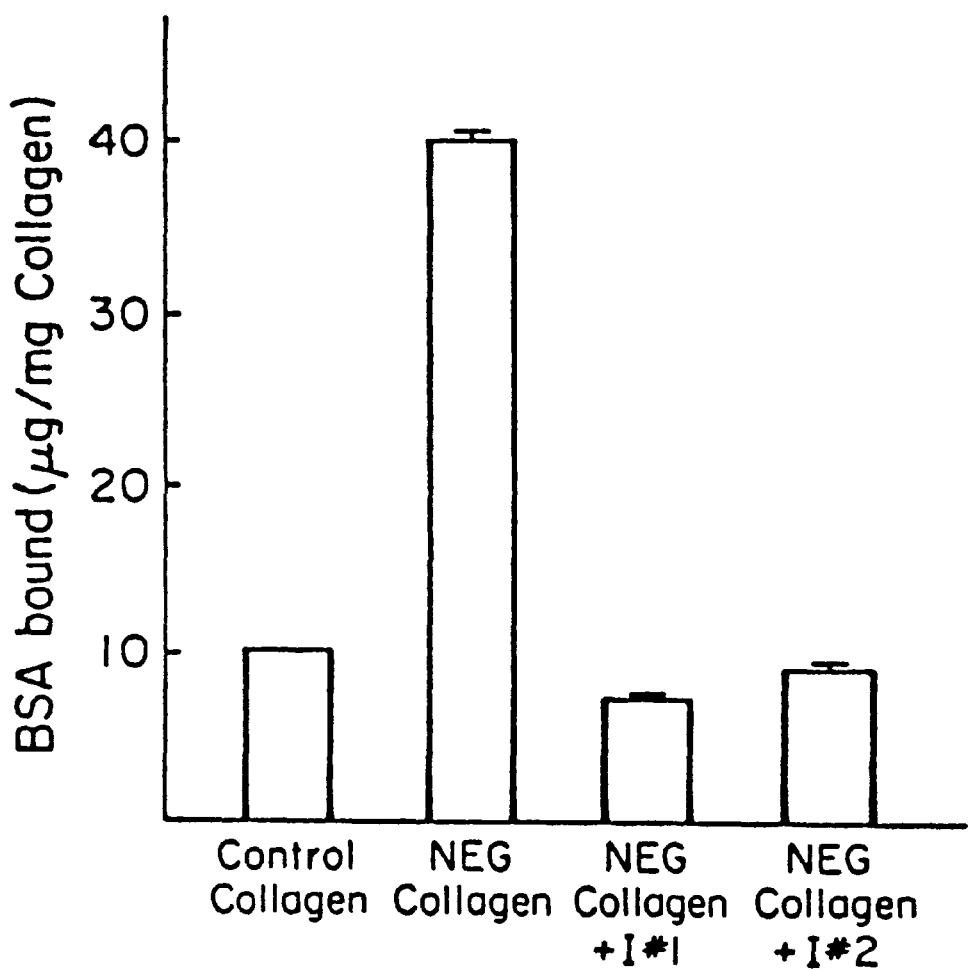
FIG. 2 is a (graph showing the results of studies aimed at inhibiting protein entrapment and accumulation by glycosylated structural proteins such as collagen.

FIG. 2 shows that the amount of protein trapping in the presence of either aminoguanidine ("NEG. COLLAGEN+ 1#2") or α-hydrazinohistidine ("NEG. COLLAGEN+I#") is greatly reduced. Lysine also reduced the amount of protein trapping to an extent similar to that of aminoguanidine (not shown). The results show the potential value of these compounds in vivo for reducing the trapping or soluble protein on to membranes and other tissues, and further evidence that these agents may be of value in reducing the pathogenesis of diabetes and aging.

EXAMPLE III

As a further evaluation of the compound aminoguanidine as a model for the prevention of protein trapping, crosslinking and formation of advanced glycosylation end products, the following experiment using calf skin collagen was performed. Collagen is a protein in the skin responsible for the suppleness of skin and crosslinking leads to wrinkling, decreased elasticity, reduced susceptibility to proteolytic degradation, and other changes.

Collagen from samples of calf skin were extracted into acetic acid and then precipitated with 0.6 M sodium chloride. These procedures removed from the solution skin collagen that was already permanently crosslinked or denatured. Native collagen fibrils were reformed by dialysis against 0.02M phosphate buffer, and these were incubated for 3 weeks at 35° C. in the presence of 140 mM glucose and with or without 200 mM aminoguanidine. After incubation, the samples were dialyzed and the degree of crosslinking was determined by two methods. First, the amount of reacted collagen which could be solubilized by treatment in 2% sodium dodecyl sulfate at 100° C. was measured.

As shown in FIG. 3A, collagen incubated with glucose and aminoguanidine was as soluble as collagen incubated in buffer alone. In contrast, collagen incubated in glucose without aminoguanidine was only 50% as soluble. This is further evidence that aminoguanidine has utility in the prevention of age-related changes in skin and other tissues.

The reacted collagen was further examined by cleaving it into fragments using cyanogen bromide treatment in formic acid. the resulting protein fragments were separated by size by sodium dodecyl sulfate-polyacrylamide gel electrophoresis. After electrophoresis the protein fragments were identified in the gel using silver staining. The gel is shown in FIG. 3B.

Figure 3B:
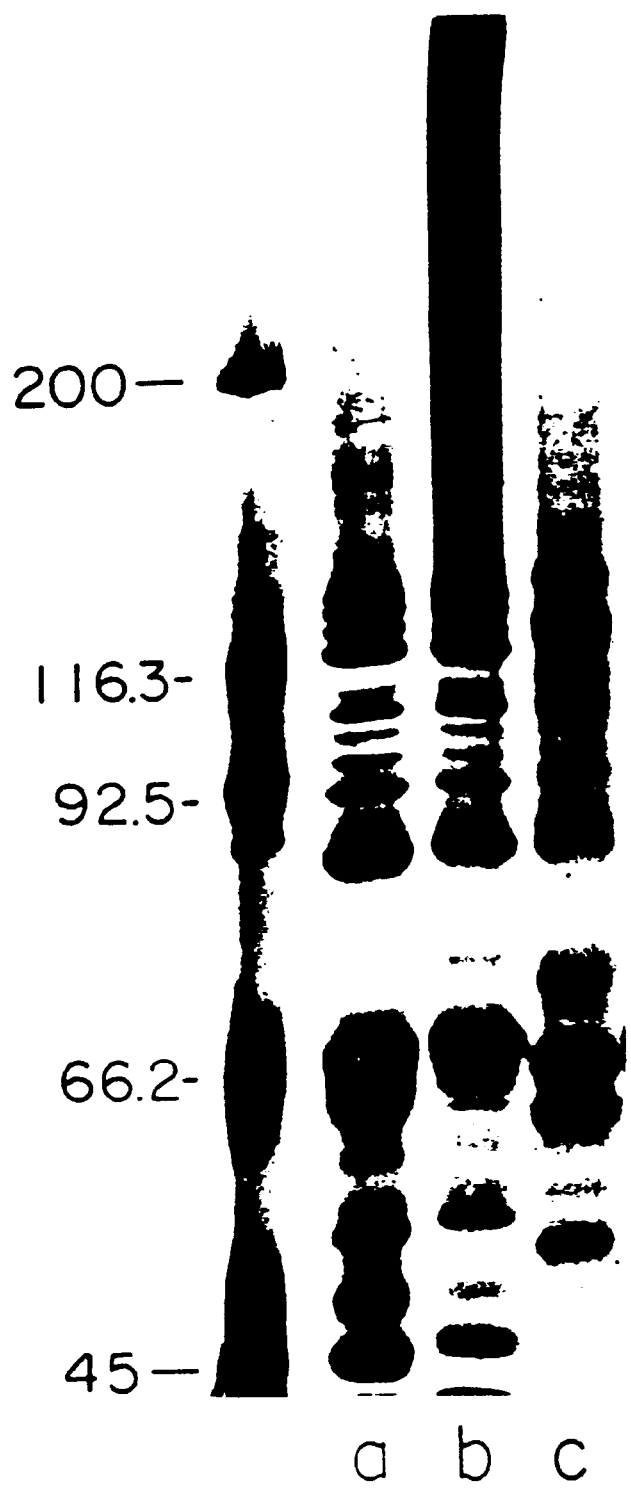
FIG. 3B is a photograph of a polyacrylamide gel showing separation of protein fragments after cyanogen bromide digestion of collagen incubated with glucose with and without an agent of the present invention.

Referring to FIG. 3B, Lane C contains collagen that was incubated with glucose alone. It is noted that a large amount of high molecular weight fragments form a continuous band at the top of the gel, indicating a large range of high molecular weight fragments. Some of this material could not enter the gel and is present in the 30% stacking gel above the gradient gel. Lane B contains the collagen incubated with glucose and aminoguanidine, and it is noted that there is no large amount of high molecular weight material at the top of the lane, as all of the protein fragments separate well in the lower part of the gel. Lanes A and D show collagen incubated in PBS alone or held frozen during the incubation of the other samples, respectively. The far left lane is a series of molecular weight markers. Identical results were observed with and without the presence of disulfide bond reducing agents in the electrophoresis buffer.

The above data indicate that aminoguanidine reduces the amount of crosslinking which occurs when collagen is incubated with glucose, and suggest the utility of this agent for topical application to skin to prevent age-related changes, including loss of elasticity and wrinkling.

The above in vitro experiments all point to the value of aminoguanidine as an agent to inhibit the formation of advanced glycosylation end products which form in vitro from proteins incubated in the presence of glucose or other reducing sugars. As glucose is present in the body and is elevated in amount in diabetes, and as proteins in the body are known to undergo crosslinking and form fluorescent compounds all indicative of advanced glycosylation end products, use of this agent in vivo would be useful in the prevention of the pathology associated with diabetes and changes that occur during aging Accordingly, the following experiment was performed to test the hypothesis of the present invention in an in vivo experiment.

EXAMPLE IV

To measure the level of advanced glycosylation end products in vivo, the kidneys of rats were examined for serum proteins which had become attached to glomerular basement membranes. This was determined to be a good model in which to study this process as it is known that significant kidney pathology occurs in untreated diabetes as a result of the buildup of extravasated plasma protein in the extravascular matrix in this organ.

The experiment consisted of giving both normal and diabetic rats daily intraperitoneal doses of the agent aminoguanidine hydrochloride at a dose of 25 mg per kilogram of body weight for a period of 16 weeks. The hydrochloride salt of aminoguanidine was used as it is more soluble and less irritating than the parent free base compound. Diabetes was induced prior to drug therapy with a single dose of streptozotocin. Control animals, both diabetic and normal, received no drug.

At the end of the agent therapy, animals were sacrificed and the kidneys were removed. Each organ was removed from its capsule and the medulla was removed. The remainder of the tissue, principally containing glomeruli, was frozen on dry ice and stored at $-70°$ C. Tissue from five animals in each treatment group was combined for processing.

To prepare glomerular basement membranes, tissue was cut into slices and passed through a series of sieves (170, 100 and 270) to separate glomeruli from tubules and other undesired tissue elements as described (Beisswenger, P. J., Spiro, R. G., *Diabetes*, 22:180–193, 1973). Glomerular purity was found to be 80–90%. The final material was collected and centrifuged at 1500 rpm for fifteen minutes to pellet the glomeruli, which were frozen at $-70°$ C.

Thawed isolated glomeruli were then disrupted by treatment in a Branson Sonifier 200 cell disrupter for four one-minute intervals on ice with a one-minute rest between sonications. Samples were examined in a phase contrast microscope to ensure that all of the glomeruli were disrupted. Glomerular basement membranes were then pelleted by centrifugation at 3000 rpm for ten minutes, washed with 1 M sodium chloride followed by distilled water. The remaining pellet of purified glomerular basement membranes was frozen and lyophilized.

An enzyme immunoassay was used to measure the amount of serum immunoglobulin G(IgG) that became bound to the glomerular basement membranes of the normal and diabetic animals after treatment with and without the agent. To measure IgG, 6 mg samples of lyophilized glomerular basement membrane tissue was suspended in 0.5 mM of 0.05 M carbonate buffer, pH 7.6, and 0.5 mM of a 1:5,000 dilution of rat anti-IgG antibody conjugated to alkaline phosphates (Dynatech Corp.) was added. The mixture was incubated overnight in polystyrene tubes which were preblocked by incubation for two hours in 3% goat serum plus 0.05% Tween 20 in phosphate buffered saline (PBS). followed by two rinses in PBS plus Tween.

After overnight incubation to allow the antibody to bind to any IgG crosslinked to the glomerular basement membranes, the membranes were pelleted by centrifugation at 3200 rpm for five minutes and were washed free of the unbound antibody-enzyme conjugate with four rinses with PBS plus Tween followed by three rinses with distilled water. To measure the amount of antibody-enzyme conjugate remaining bound, 0.5 mM of substrate solution (containing 1 mg/mL para-nitrophenylphosphate in 10% diethanolomaine, pH 9.8), was added and incubations were carried out for 30 minutes at room temperature. The reaction was stopped with the addition of 0.2 mL of M sodium hydroxide, and the absorbance at 400 nm was measured.

Figure 4:
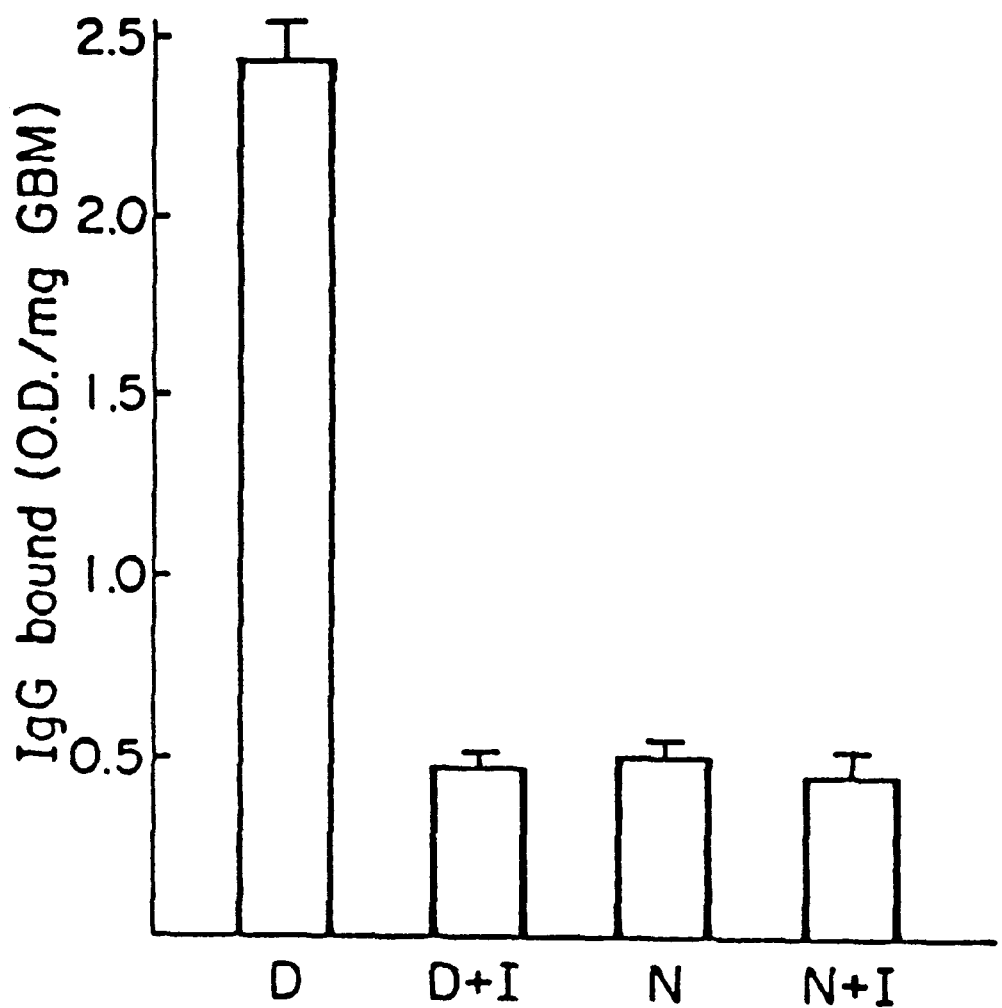
FIG. 4 is a graph of the results of an in vivo study examining the extent of protein bound to the glomerular basement membrane of diabetic rats to certain of which an agent of the present invention had been administered.

FIG. 4 shows the results of this experiment. As can be seen, diabetic animals had a high level of IgG bound to their glomerular basement membranes ("D") and normal animals had about one-fifth the amount ("N"). Diabetic animals which received daily doses of aminoguanidine hydrochloride showed the same low level of IgG in normal animals ("D+I"). Normal animals receiving the drug had about the same low level ("N+I").

These experiments indicated that aminoguanidine prevented the trapping and accumulation of this plasma protein on the rat glomerular basement membranes. Presumably, the trapping of this and other serum proteins in the kidney, eye, on artery walls, and in other tissues known to be affected from this pathology would likewise be reduced. Trapping of lipoproteins on artery walls is known to contribute to atherosclerotic disease.

These in vivo experiments provide further evidence from the in vitro experiments that this type of drug therapy has benefit in reducing the pathology associated with the advanced glycosylation of proteins and the formation of crosslinks between proteins and other macromolecules. Drug therapy may be used to prevent the increased trapping and crosslinking of proteins that occurs in diabetes and aging which leads to sequela such as arterial disease, including renal disease, hypertension, retinal damage, and extravascularly, damage to tendons, ligaments and other joints. This therapy might retard atherosclerosis and connective tissue changes that occur with diabetes and aging. Both topical, oral and parenteral routes of administration to provide therapy locally and systematically are contemplated.

EXAMPLE V

Aorta samples from the same groups of animals described in Example IV above were subjected to analysis for Advanced Glycosylation Endproducts (A.G.E.) content and solubility.

Aortas were finely minced with dissecting scissors, delipidated with 5 mL of chloroform: methanol (2:1). washed 5 times with buffer, and divided into aliquots for the following assessments of cross-linking:

(A) Specific fluorescence of collagen after complete solubilization by proteinase k and pepsin.

(B) Solubility in 0.5M acetic acid was determined after 2 hours of extraction at 25° C. and 24 hours at 4° C.

(C) Solubility after cyanogen bromide cleavage at 30° C. for 18 hours was determined.

(D) Solubility after degradation by pepsin (1.0 mg/mL) in 0.1M acetate buffer, pH 4.1, at 37° C. for 48 hours.

After treatment for the prescribed period, soluble material was separated from insoluble material by centrifugation (50.000× g, 1 hour), and all fractions were lyophilized and hydrolyzed in 6M HCl for determination of total hydroxyproline. The results of these analyses are set forth in Table 1, below.

TABLE I

Percent collagen solubilized by:

| Group | Treatment | Advanced glycosylation products* | 0.5 M acetic acid | CNBr | Pepsin |
|---|---|---|---|---|---|
| Normal | None | 3.5 ± 0.11 | 8.0 ± 0.3 | 12.2 ± 0.1 | 50.9 ± 0.3 |
| Diabetic | None | 19.4 ± 0.8 | 2.0 ± 0.2 | 4.4 ± 0.1 | 15.0 ± 0.2 |
| Normal | Aminoguanidine | 2.8 ± 0.1 | 18.7 ± 0.3 | 13.6 ± 0.3 | 52.5 ± 0.2 |
| Diabetic | Aminoguanidine | 4.5 ± 0.1 | 12.6 ± 0.3 | 10.6 ± 0.1 | 46.1 ± 0.4 |

*Specific fluorescence per mg hydroxyproline

As can be seen from Table I, accumulation of fluorescent advanced nonenzymatic glycosylation products in aortic connective tissue from untreated diabetic rats was 5.5 times greater than that in aortic tissue from untreated normal rats. In contrast, the level in aortic tissue from aminoguanidine-treated diabetic rats was only 1.3 times that of untreated normal rats, despite exposure to identical levels of hyperglycemia for the same period of time. These data indicate that accumulation of advanced nonenzymatic glycosylation products is inhibited by aminoguanidine in vivo.

The percentage of aortic connective tissue solubilized by each of the three specified procedures (acetic acid, CNBr, and pepsin) was significantly reduced in samples from untreated diabetic animals compared to those from normal animals. Diabetic aortic connective tissue from untreated rats was 9 times more cross-linked than normal as assessed by acetic acid solubility, 2.8 times more as assessed by CNBr digestion, and 3.4 times as cross-linked according to pepsin digestibility.

In contrast, aortic connective tissue from aminoguanidine-treated diabetic animals was only 1.1 to 1.4 times more cross-linked than normal despite exposure to identical levels of hyperglycemia for the same period of time. These data indicate that aminoguanidine prevents hyperglycemia-induced increases in nonenzymatic collagen cross-linking in vivo.

EXAMPLE VI

Aorta samples from the same group of animals described in Example IV above, were subjected to analysis for cross-linking of lipoprotein to collagen, using an enzyme immunoassay. A standard ELISA procedure was employed, using antiserum to rat apoliproprotein-B raised in rabbits, peroxidase-labeled anti-rabbit antibody, and standard chromogenic reagents to detect quantity of antibody bound.

The results are set forth in Table II, below.

TABLE II

| TREATMENT GROUP COLLAGEN | LIPOPROTEIN BOUND PER MG |
|---|---|
| Normal | 0.69 |
| Diabetic | 1.86 |
| Normal + Aminoguanidine | 0.53 |
| Diabetic + Aminoguanidine | 0.64 |

These data indicate that lipoprotein accumulation in the macrovasculature, an early event in the atherogenic process, may be treatable by aminoguanidine administration.

EXAMPLE VII

In order to assess the possible role of hyperglycemia-induced matrix modifications in this process, demineralized bone matrix particles from 35 week old normal Long-Evans rats were prepared. Matrix is incubated in phosphate buffered saline alone (PBS), PBS containing various sugar precursors of AGE (PBS-G), and PBS with sugars plus the AGE-inhibitor aminoguanidine (PBS-G+AG). After incubation, the matrix is washed and implanted subcutaneously in normal rats. Twelve days after implantation, $^{45}CaCl_2$ is injected to determine implant mineralization, and alkaline phosphatase activity is measured to assess osteoblast function. Duplicate specimens are fixed, embedded and stained for histologic evaluation.

The AGE precursor glycolaldehyde increased the matrix AGE content (by specific fluorescence) over twofold, while inhibiting bone differentiation more than 90% ($^{45}CaCl_2$ uptake, alk phos, and histology). In contrast, simultaneous incubation with the AGE-inhibitor aminoguanidine reduced fluorescence to normal, and restored bone differentiation to 80% of control.

EXAMPLE VIII

New Zealand white rabbits, with induced, long-term diabetes (12.7±3.2 months) are used to study the effects of a test compound on red blood cell (RBC) deformability. If glucose-mediated crosslinking of red blood cell components results in less deformable, more rigid membrane then therapy should prevent this change in new red cells. Red blood cells already in existence at the initiation of therapy would be unaffected; because RBCs are replaced frequently newly formed red blood cells would be exposed to the therapy. The diabetic rabbits (n=6) had a mean blood sugar of 292.6±84.6 mg/dl before and after a two-month dosage regimen. The test compound is administered at a rate of 100 mg/kg/day by oral gavage.

The deformability index (DI) (filtration rate of buffer/filtrate rate of suspended RBCs; hematocrit=4.0%) is used as a measure of RBC deformability. Buffer and suspended RBCs are filtered through a 3µ micropore membrane (Nucleopore Corp., Pleasanton, Calif.) with a pressure of −20 cm $H_2$ at 37° C. A reference range for RBC deformability (2.67 to 4.84, mean 4.02±0.69) and % hemoglobin glycosylation (1.7 to 3.96, mean 2.60±0.70) is obtained from a group of normal New Zealand white rabbits (n=14), matched for age, sex and weight.

The results are given in Table III, below for diabetic New Zealand white rabbits dosed with 100 mg/kg/day aminoguanidine.

TABLE III

Red Blood Cell Deformability of Long-Term
Diabetic Rabbits on Aminoguanidine HCl

| Duration of Dosing (weeks) | Red Blood Cell Deformability Index |
|---|---|
| 0 | 18.32 ± 6.03 |
| 4 | 7.17 ± 3.12 |
| 8 | 6.83 ± 2.97 |
| 12 | 4.64 ± 1.58 |
| 16 | 4.44 ± 1.33 |
| 20 | 4.14 ± 1.06 |

Diabetes causes an increase in the deformability index from 4.0 to 18. The results show that aminoguanidine administration reduces the diabetes-induced decreased deformability (increased deformability index) value to normal after 12 weeks. In a separate experiment, aminoguanidine hydrochloride was administered daily to rabbits at the time of induction of diabetes. The RBC deformability index in these animals never became abnormal. These experiments indicate that aminoguanidine prevents diabetes-induced RBC deformability changes; the rabbits with delayed treatment showed positive effect over time presumably as old red cells, which already had been cross-linked and were less deformable, were replaced with new red cells under the influence of aminoguanidine to inhibit cross-linking.

EXAMPLE IX

Streptozotocin-diabetic male Lewis rats were treated for a 9-month time period with daily doses of aminoguanidine hydrochloride of 0, 6.25 12.5, 25, and 50 mg/kg/day. After the treatment period, collagen in tail tendon fiber was subjected to solubility determination. Ten mg samples were incubated with gentle rocking for 5 hours at 4° C. in 5 ml of 0.5M acetic acid containing 1 mg pepsin. The samples were then centrifuged at 50,000× g for 1 hour, and the soluble and insoluble fraction separated by decanting. Each fraction was hydrolyzed in 6N HCl and total hydroxyproline measured. The results are set forth in Table IV, below.

TABLE IV

| Condition | Aminoguanidine HCl mg/kg/day | Collagen Solubility |
|---|---|---|
| Normal | 0 | 80.7 ± 3.4% |
| Diabetic | 0 | 64.8 ± 0.8% |
| Diabetic | 12.5 | 66.7 ± 1.2% |
| Diabetic | 50 | 75.9 ± 0.4% |
| Normal | 50 | 88.2 ± 0.2% |

Diabetes of 9 months duration reduced tail tendon collagen solubility from 91% to 8%. Administration of AG HCl at doses from 6.25 up to 50 mg/kg/day orally significantly prevented this change in a dose-dependent manner with the highest dose preventing 80% of the diabetes induced cross-linking.

EXAMPLE X

The effect of aminoguanidine administration on collagen cross-linking was examined in a genetically-diabetic animal model, the BB/Worcester rat. Once the animals become diabetic, daily insulin injections are essential for survival. Glucose levels are maintained at a moderate level (250–350 mg %), much lower than in the streptozotocin-diabetic animals (>500 mg %).

Diabetic and non-diabetic controls were treated orally with aminoguanidine hydrochloride at 12.5 and 50 mg/kg/day for 6 months. Control animals were dosed with water only. Tail tendon collagen solubility was then determined by the pepsin method described in Example IX.

The results are set forth in Table V, below.

TABLE V

| Condition | Aminoguanidine HCl mg/kg/day | Collagen Solubility |
|---|---|---|
| Normal | 0 | 80.7 ± 3.4% |
| Diabetic | 0 | 64.8 ± 0.8% |
| Diabetic | 12.5 | 66.7 ± 1.2% |
| Diabetic | 50 | 75.9 ± 0.4% |
| Normal | 50 | 88.2 ± 0.2% |

These data show that the solubility of tail tendon collagen was reduced from 81% to 65% with diabetes of 6 months' duration but prevented significantly, in a dose-dependent manner, by both aminoguanidine treatments. Diabetic BB/Worcester rat collagen showed less decrease in solubility over the 6 month period than streptozotocin-diabetic rats presumably because of the lower degree of hyperglycemia and lower concentration of glucose to which collagen was exposed chronically.

This invention may be embodied in other forms or carried out in other ways without department from the spirit or essential characteristics thereof. The present disclosure is therefor to be considered as in all respects illustrative and not restrictive, the scope of the invention being indicated by the appended claims, and all changes which come within the meaning and range of equivalency are intended to be embraced therein.

What is claimed is:

1. A method of treating diabetic kidney disease comprising administering an effective amount of a pharmaceutical composition comprising an agent selected from the group consisting of aminoguanidine, its pharmaceutically acceptable salts, and mixtures thereof, to treat diabetic kidney disease.

2. The method of claim 1, wherein said aminoguanidine is selected from the group consisting of aminoguanidine hydrochloride, aminoguanidine bicarbonate, aminoguanidine sulfate and mixtures thereof.

3. The method of claim 1, wherein said pharmaceutical composition is administered parenterally or orally.

4. A method of treating diabetic retinopathy comprising administering an effective amount of a pharmaceutical composition comprising an agent selected from the group consisting of aminoguanidine, its pharmaceutically acceptable salts, and mixtures thereof, to treat diabetic retinopathy.

5. The method of claim 4, wherein said aminoguanidine is selected from the group consisting of aminoguanidine hydrochloride, aminoguanidine bicarbonate, aminoguanidine sulfate and mixtures thereof.

6. The method of claim 4, wherein said pharmaceutical composition is administered parenterally or orally.

7. A method of treating a complication of diabetes comprising administering an effective amount of an agent selected from the group consisting of aminoguanidine, its pharmaceutically acceptable salts, and mixtures thereof.

8. The method of claim 7, wherein said aminoguanidine is selected from the group consisting of aminoguanidine hydrochloride, aminoguanidine bicarbonate, aminoguanidine sulfate and mixtures thereof.

9. The method of claim 7, wherein said pharmaceutical composition is administered parenterally or orally.

10. A method of treating diabetic kidney disease comprising administering an effective diabetic kidney disease pathology reducing amount of an agent selected from the group consisting of aminoguanidine, its pharmaceutically acceptable salts, and mixtures thereof.

11. The method of claim 10 wherein said diabetic kidney disease pathology is selected from the group consisting of proteinuria, glomerular basement membrane thickening, mesangial expansion, extravasation of serum proteins, trapping of serum proteins, and decreased creatinine clearance.

12. The method of claim 10, wherein said aminoguanidine is selected from the group consisting of aminoguanidine hydrochloride, aminoguanidine bicarbonate, aminoguanidine sulfate and mixtures thereof.

13. The method of claim 10 wherein said agent is administered parenterally or orally.

14. A method of treating diabetic retinopathy comprising administering a diabetic retinopathy pathology reducing amount of an agent selected from the group consisting of aminoguanidine, its pharmaceutically acceptable salts, and mixtures thereof.

15. The method of claim 14 wherein said diabetic retinopathy pathology is selected from the group consisting of extravasation of serum proteins and trapping of serum proteins.

16. The method of claim 14 wherein said aminoguanidine is selected from the group consisting of aminoguanidine hydrochloride, aminoguanidine bicarbonate, aminoguanidine sulfate and mixtures thereof.

17. The method of claim 14, wherein said agent is administered parenterally or orally.

18. A method of treating diabetic kidney disease comprising administering an effective glomerular basement membrane thickening inhibiting amount of an agent selected from the group consisting of aminoguanidine, its pharmaceutically acceptable salts, and mixtures thereof.

19. The method of claim 18, wherein said aminoguanidine is selected from the group consisting of aminoguanidine hydrochloride, aminoguanidine bicarbonate, aminoguanidine sulfate and mixtures thereof.

20. The method of claim 18, wherein said pharmaceutical composition is administered parenterally or orally.

21. A method of treating diabetic kidney disease comprising administering an effective plasma protein extravasation inhibiting amount of an agent selected from the group consisting of aminoguanidine, its pharmaceutically acceptable salts, and mixtures thereof.

22. The method of claim 21, wherein said aminoguanidine is selected from the group consisting of aminoguanidine hydrochloride, aminoguanidine bicarbonate, aminoguanidine sulfate and mixtures thereof.

23. The method of claim 21, wherein said pharmaceutical composition is administered parenterally or orally.

24. A method of treating diabetic kidney disease comprising administering an effective proteinuria inhibiting amount of an agent selected from the group consisting of aminoguanidine, its pharmaceutically acceptable salts, and mixtures thereof.

25. The method of claim 24, wherein said aminoguanidine is selected from the group consisting of aminoguanidine hydrochloride, aminoguanidine bicarbonate, aminoguanidine sulfate and mixtures thereof.

26. The method of claim 24, wherein said pharmaceutical composition is administered parenterally or orally.

27. A method of treating diabetic retinopathy comprising administering an effective serum protein extravasation reducing amount of an agent selected from the group consisting of aminoguanidine, its pharmaceutically acceptable salts, and mixtures thereof.

28. The method of claim 27 wherein said aminoguanidine is selected from the group consisting of aminoguanidine hydrochloride, aminoguanidine bicarbonate, aminoguanidine sulfate and mixtures thereof.

29. The method of claim 27, wherein said agent is administered parenterally or orally.

30. A method of treating diabetic retinopathy comprising administering an effective serum protein trapping reducing amount of an agent selected from the group consisting of aminoguanidine, its pharmaceutically acceptable salts, and mixtures thereof.

31. The method of claim 30 wherein said aminoguanidine is selected from the group consisting of aminoguanidine hydrochloride, aminoguanidine bicarbonate, aminoguanidine sulfate and mixtures thereof.

32. The method of claim 30, wherein said agent is administered parenterally or orally.

* * * * *